US00PP24256P2

(12) United States Plant Patent
van der Hoorn

(10) Patent No.: US PP24,256 P2
(45) Date of Patent: Feb. 18, 2014

(54) ***HAWORTHIA* PLANT NAMED 'AFRICAN ALBINO'**

(50) Latin Name: *Haworthia fasciata*
Varietal Denomination: African Albino

(75) Inventor: Antonius C. J. van der Hoorn, Nieuwveen (NL)

(73) Assignee: T.H. Primeur B.V., Nieuwveen (NL)

( * ) Notice: Subject to any disclaimer, the term of this patent is extended or adjusted under 35 U.S.C. 154(b) by 96 days.

(21) Appl. No.: 13/506,079

(22) Filed: Mar. 24, 2012

(51) Int. Cl.
*A01H 5/00* (2006.01)

(52) U.S. Cl.
USPC ..... Plt./373; Plt./263.1

(58) Field of Classification Search
USPC ..... Plt./263.1, 373
See application file for complete search history.

*Primary Examiner* — Susan McCormick Ewoldt
(74) *Attorney, Agent, or Firm* — C. A. Whealy

(57) ABSTRACT

A new and distinct cultivar of *Haworthia* plant named 'African Albino', characterized by its upright and outwardly spreading foliage with upright flower scapes; dark green-colored leaves with white-colored spots on the upper surface and broad white-colored bands on the lower surface of the leaves; and white and yellow green-colored flowers that are positioned above the foliar plane on moderately strong scapes.

3 Drawing Sheets

Botanical designation: *Haworthia fasciata.*
Cultivar denomination: 'AFRICAN ALBINO'.

BACKGROUND OF THE INVENTION

The present invention relates to a new and distinct cultivar of *Haworthia* plant, botanically known as *Haworthia fasciata* and hereinafter referred to by the name 'African Albino'.

The new *Haworthia* plant is a naturally-occurring whole plant mutation of the *Haworthia fasciata* 'Big Band', not patented. The new *Haworthia* plant was discovered and selected by the Inventor from within a population of plants of 'Big Band' in a controlled greenhouse environment in Nieuwveen, The Netherlands in July, 2005.

Asexual reproduction of the new *Haworthia* plant by cuttings in a controlled greenhouse environment in Nieuwveen, The Netherlands since July, 2006 has shown that the unique features of this new *Haworthia* plant are stable and reproduced true to type in successive generations.

SUMMARY OF THE INVENTION

Plants of the new *Haworthia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'African Albino'. These characteristics in combination distinguish 'African Albino' as a new and distinct *Haworthia* plant:

1. Upright and outwardly spreading foliage with upright flower scapes.
2. Dark green-colored leaves with white-colored spots on the upper surface and broad white-colored bands on the lower surface of the leaves.
3. White and yellow green-colored flowers that are positioned above the foliar plane on moderately strong scapes.

Plants of the new *Haworthia* differ primarily from plants of the parent, 'Big Band', primarily in leaf color as the lower surfaces of leaves of plants of the new *Haworthia* have broader white-colored bands than the lower surfaces of leaves of plants of 'Big Band'. In addition, plants of the new *Haworthia* are smaller than plants of 'Big Band'.

Plants of the new *Haworthia* can also be compared to plants of 'Concolor', not patented. Plants of the new *Haworthia* and 'Concolor' differ primarily in leaf color as the lower surfaces of leaves of plants of the new *Haworthia* have broad white-colored bands whereas the lower surfaces of leaves of plants of 'Concolor' are spotted.

BRIEF DESCRIPTION OF THE PHOTOGRAPHS

The accompanying colored photographs illustrate the overall appearance of the new *Haworthia* plant showing the colors as true as it is reasonably possible to obtain in colored reproductions of this type. Colors in the photographs may differ slightly from the color values cited in the detailed botanical description which accurately describe the colors of the new *Haworthia* plant.

The photograph on the first sheet comprises a side perspective view of a typical flowering plant of 'African Albino' grown in a container.

The photograph on the second sheet is a close-up view of a typical plant of 'African Albino' showing the lower surfaces of the leaves.

The photograph on the third sheet is a close-up view of a typical flowering stem of 'African Albino'.

DETAILED BOTANICAL DESCRIPTION

The aforementioned photographs and following observations, measurements and values describe plants grown during the late summer and early autumn in 8-cm containers in a glass-covered greenhouse in Nieuwveen, The Netherlands and under commercial practices. During the production of the plants, day temperatures averaged 15° C. and night temperatures averaged 12° C. Plants were eight months old when the photographs and description were taken. In the following description, color references are made to The Royal Horticultural Society Colour Chart, 2007 Edition, except where general terms of ordinary dictionary significance are used.

Botanical classification: *Haworthia fasciata* 'African Albino'.

Parentage: Naturally-occurring whole plant mutation of the *Haworthia fasciata* 'Big Band', not patented.

Propagation:

*Type*.—By cuttings.

*Time to initiate roots, summer*.—About 35 days at 22° C. to 23° C.

*Time to initiate roots, winter*.—About 50 days at 12° C. to 15° C.

*Time to produce a rooted young plant, summer*.—About 25 weeks at 22° C. to 23° C.

*Time to produce a rooted young plant, winter*.—About 30 weeks at 12° C. to 15° C.

*Root description*.—Thick, fleshy; white to creamy white in color.

*Rooting habit*.—Sparse.

Plant description:

*Plant form and growth habit*.—Herbaceous flowering perennial plant; basal rosette plant form with upright to outwardly spreading foliage and upright flower scapes; dark green-colored leaves with white-colored spots on the upper surface and broad white-colored bands on the lower surface of the leaves; white and yellow green-colored flowers that are positioned above the foliar plane on moderately strong scapes; low vigor.

*Plant height* (*soil level to top of foliar plane*).—About 9.8 cm.

*Plant height* (*soil level to top of inflorescences*).—About 29.7 cm.

*Plant width* (*leaves only*).—About 11.2 cm.

*Plant width* (*with inflorescence*).—About 20.4 cm.

Foliage description:

*Arrangement and quantity*.—Leaves arranged in a basal rosette, simple, generally symmetrical and long-persisting; leaves sessile.

*Leaf length*.—About 7.2 cm.

*Leaf width*.—About 1.9 cm.

*Shape*.—Subulate.

*Apex*.—Narrowly acute.

*Base*.—Broadly cuneate.

*Margin*.—Entire.

*Texture, upper and lower surfaces*.—Glabrous; succulent; strongly verrucose, rough.

*Venation pattern*.—Parallel.

*Color*.—Developing leaves, upper surface: Close to 137A to 137B; towards the base, close to 138B; spots and margins, close to NN155D. Developing leaves, lower surface: Close to 137A; towards the base, close to between 138A and 137B; broad bands and margins, close to NN155D. Fully expanded leaves, upper surface: Close to N137B; towards the base, close to 189A; spots and margins, close to NN155D; venation, similar to leaf surface color. Fully expanded leaves, lower surface: Slightly darker than between N137A and 147A; broad bands and margins, close to NN155D; venation, similar to leaf surface color.

Flower description:

*Flower type and flowering habit*.—Single campanulate flowers with fused perianth arranged on terminal simple or compound racemes; flowers face mostly outwardly; freely flowering habit with about 14 flowers per simple raceme and about 40 flowers per compound raceme.

*Fragrance*.—None detected.

*Natural flowering season*.—Flowering continuous from mid-summer to mid-autumn in The Netherlands.

*Postproduction longevity*.—Flowers last about five days on the plant; flowers not persistent.

*Flower buds*.—Height: About 1.3 cm. Diameter: About 2 mm. Shape: Narrowly oblong. Color: Close to NN155B; stripes, close to 147C; towards the base, close to 145C; towards the apex, tinged with close to 179C to 179D.

*Inflorescence height, simple racemes*.—About 10.8 cm.

*Inflorescence height, compound racemes*.—About 20.4 cm.

*Inflorescence width, simple racemes*.—About 3 cm.

*Inflorescence width, compound racemes*.—About 15.7 cm.

*Flower diameter*.—About 10 mm by 7 mm.

*Flower depth*.—About 1.4 cm.

*Perianth*.—Arrangement: Three tepals pointed upright and three tepals pointed downward fused in a tube. Tepal length: About 1.5 cm. Tepal width: About 2 mm. Tepal shape: Narrowly oblong. Tepal apex: Obtuse. Tepal margin: Entire. Tepal texture, upper and lower surfaces: Smooth, glabrous; velvety. Tepal color: Developing and fully expanded petals, upper surface: Lobe, close to NN155B with stripes, close to 146B; towards the apex, tinged with close to 179D; throat, close to 146B to 146C. Developing and fully expanded petals, lower surface: Close to NN155B with stripes, close to 147C; towards the apex, tinged with close to 179D.

*Peduncles* (*scapes*).—Length: About 16.7 cm. Diameter: About 1.5 mm. Strength: Moderately strong. Texture: Smooth, glabrous. Color: Close to 146A.

*Pedicels*.—Length: About 4 mm. Diameter: About 0.75 mm. Strength: Moderately strong. Texture: Smooth, glabrous. Color: Close to 152A.

*Reproductive organs*.—Stamens: Quantity per flower: Typically six. Filament length: About 5 mm. Filament color: Close to 145C. Anther shape: Reniform. Anther length: About 0.5 mm. Anther color: Close to 24A. Pollen amount: Scarce. Pollen color: Close to 11D. Pistils: Quantity per flower: One. Style length: About 1.75 mm. Style color: Close to 150B to 150C. Stigma shape: Flattened. Stigma color: Close to 150B. Ovary color: Close to 144A.

*Seeds and fruits*.—Seed and fruit development have not been observed on plants of the new *Haworthia*.

Disease & pest resistance: Plants of the new *Haworthia* have not been noted to be resistant to pathogens and pests common to *Haworthia* plants.

Temperature tolerance: Plants of the new *Haworthia* have been observed to tolerate high temperatures of about 45° C. and to be hardy to USDA Hardiness Zone 10.

It is claimed:

1. A new and distinct *Haworthia* plant named 'African Albino' as illustrated and described.

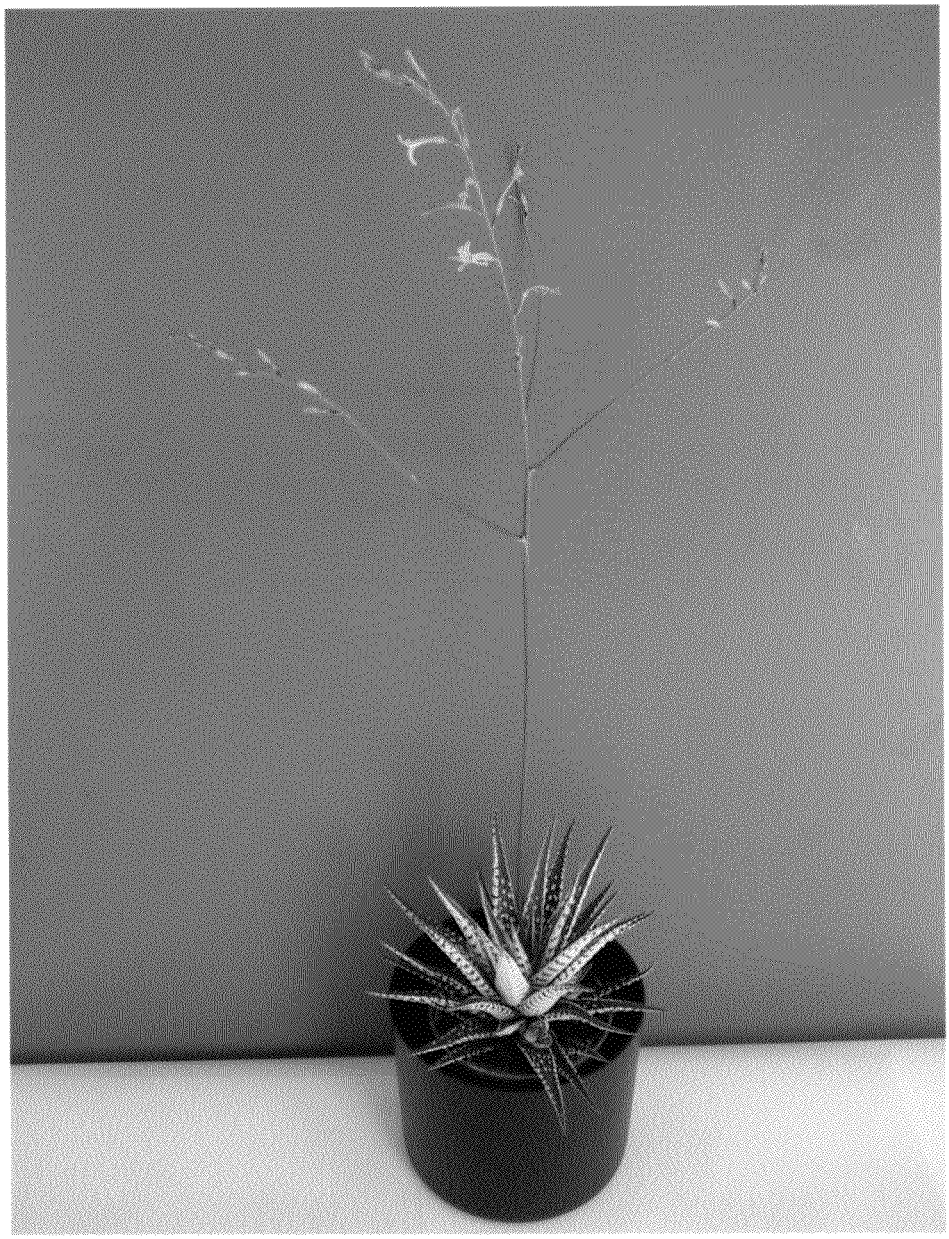

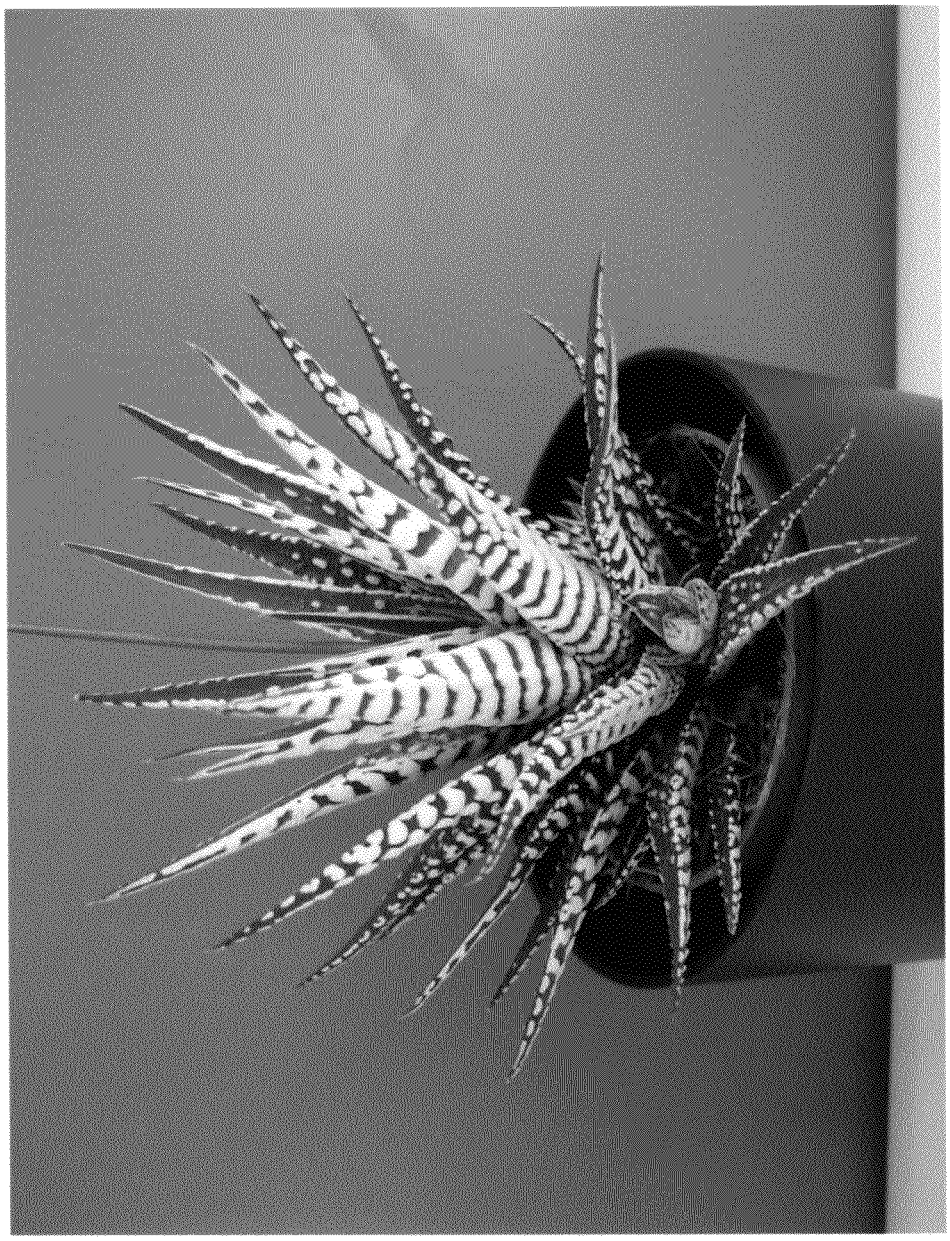

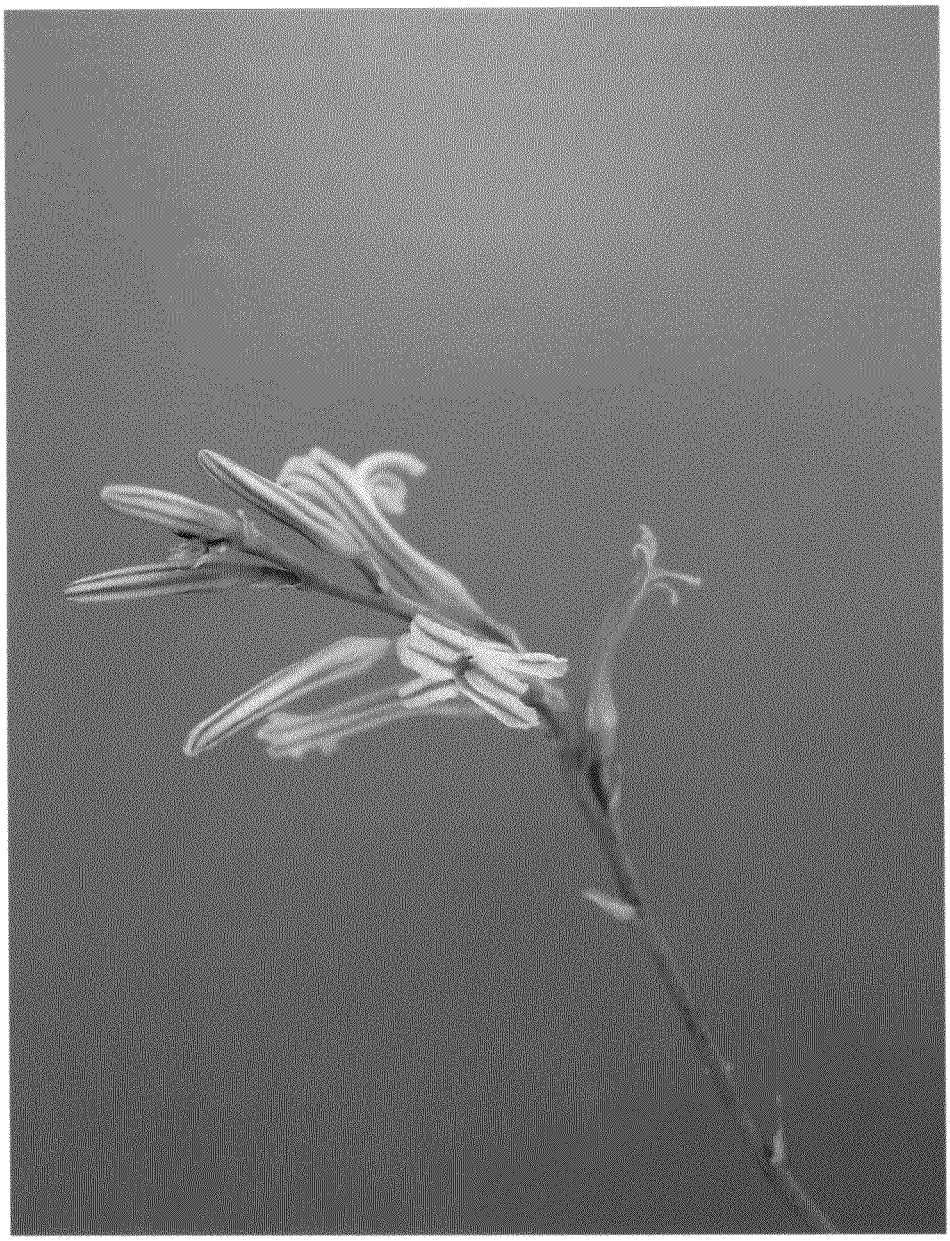

* * * * *